US006528067B1

(12) United States Patent
Magdassi et al.

(10) Patent No.: US 6,528,067 B1
(45) Date of Patent: Mar. 4, 2003

(54) TOTAL NUTRIENT ADMIXTURES AS STABLE MULTICOMPONENT LIQUIDS OR DRY POWDERS AND METHODS FOR THE PREPARATION THEREOF

(75) Inventors: Shlomo Magdassi, Jerusalem (IL); Andrew Yang, Rosemead, CA (US); Chunlin Tao, Beverly Hills, CA (US); Neil P. Desai, Los Angeles, CA (US); Zhiwen Yao, Culver City, CA (US); Patrick Soon-Shiong, Los Angeles, CA (US)

(73) Assignee: American Bioscience, Inc., Santa Monica, CA (US)

( * ) Notice: Subject to any disclaimer, the term of this patent is extended or adjusted under 35 U.S.C. 154(b) by 0 days.

(21) Appl. No.: 09/457,085

(22) Filed: Dec. 7, 1999

Related U.S. Application Data

(60) Continuation-in-part of application No. 08/412,726, filed on Mar. 29, 1995, now Pat. No. 5,560,933, which is a division of application No. 08/023,698, filed on Feb. 22, 1993, now Pat. No. 5,439,686.

(51) Int. Cl.$^7$ .......................... A61K 39/02; A61K 9/14; C08J 9/28

(52) U.S. Cl. .......................... 424/264; 424/489; 521/65
(58) Field of Search .......................... 252/316; 208/516; 521/65; 424/264

(56) References Cited

U.S. PATENT DOCUMENTS

| | | | |
|---|---|---|---|
| 3,959,457 A | 5/1976 | Speaker et al. | |
| 4,073,943 A | 2/1978 | Wretlind et al. | |
| 4,247,406 A | 1/1981 | Widder et al. | |
| 4,357,259 A | * 11/1982 | Senyei et al. | 252/316 |
| 4,572,203 A | 2/1986 | Feinstein | |
| 4,671,954 A | 6/1987 | Goldberg et al. | |
| 4,718,433 A | 1/1988 | Feinstein | |
| 4,789,550 A | 12/1988 | Hommel et al. | |
| 4,844,882 A | 7/1989 | Widder et al. | |
| 5,110,606 A | 5/1992 | Geyer et al. | |
| 5,362,478 A | 11/1994 | Desai et al. | 424/9 |
| 5,439,686 A | 8/1995 | Desai et al. | 424/451 |
| 5,498,421 A | 3/1996 | Grinstaff et al. | 424/450 |
| 5,505,932 A | 4/1996 | Grinstaff et al. | 424/9.3 |
| 5,508,021 A | 4/1996 | Grinstaff et al. | 424/9.322 |
| 5,512,268 A | 4/1996 | Grinstaff et al. | 424/9.322 |
| 5,560,933 A | 10/1996 | Soon-Shing et al. | 424/489 |

FOREIGN PATENT DOCUMENTS

| | | |
|---|---|---|
| EP | 0 129 619 A1 | 1/1985 |
| EP | 0 295 941 A2 | 12/1988 |
| EP | 0 391 518 A2 | 2/1990 |
| EP | 0 361 677 A1 | 4/1990 |
| EP | 0 418 153 A1 | 3/1991 |
| EP | 0 190 050 B1 | 5/1991 |
| EP | 0 213 303 B1 | 9/1991 |
| WO | WO 85/00011 | 1/1985 |
| WO | WO 87/01035 | 2/1987 |
| WO | WO 88/01506 | 3/1988 |
| WO | WO 88/07365 | 10/1988 |
| WO | WO 89/03674 | 5/1989 |
| WO | WO 90/13285 | 11/1990 |
| WO | WO 90/13780 | 11/1990 |
| WO | WO 91/15947 | 10/1991 |

OTHER PUBLICATIONS

Brown et al. "Total Nutrient Admixture: A Review", 1986 Journal of Parenteral and Enteral Nutrition, pp. 650–658.*

Scatchard, et al. "Chemical, Clinical, and Immunolgoical Studies on the Products of Human Plasma Fractionation: A Study of the Thermal Stability of Human Serum Albumin", 1944, pp. 445–453.*

Brown et al., "Effect of albumin supplementation during parenteral nutrition on hospital morbidity" *Critical Care Medicine*, 16:1177–1182 (1988).

Magdassi et al., "Chemical Instability of Phosholipids: A Key Factor in Stabilization of Perfluorocarbon Emulsions" *J. Disp. Sci. Tech.*, 12(1):69–82 (1991).

Burgess et al., "Potential use of albumin microspheres as a drug delivery system. I. Preparation and in vitro release of steroids," *International Journal of Pharmaceutics*, 39:129–136 (1987).

(List continued on next page.)

*Primary Examiner*—Jose' G. Dees
*Assistant Examiner*—R. DeWitty
(74) *Attorney, Agent, or Firm*—Stephen E. Reiter; Foley & Lardner

(57) ABSTRACT

In accordance with the present invention, there are provided stabilized total nutrient admixture (TNA) compositions which are useful for the in vivo parenteral delivery of pharmacologically acceptable lipids or fats, as well as methods for the preparation thereof. In particular, the pharmacologically acceptable lipid or fat is contained within a protein walled shell. In a particular embodiment of the invention, a TNA composition using human serum albumin (HSA) as a stabilizer has been prepared as a convenient three-in-one formulation (i.e., containing a fat emulsion, dextrose, and amino acids plus electrolytes). This "three-in-one" formulation can be prepared in liquid form or in dry form (comprising submicron-sized nanoparticles). The dried material is stable, even under long term storage, and is easily reconstituted immediately before use by simply adding sterile water (with or without vitamin supplementation) This serves to rehydrate the powder into a TNA suitable for injection. The long shelf life, ease of reconstitution, and single-component injectability of invention compositions provide significant cost savings, as such compositions can be reconstituted and administered safely, even in the home. In addition, HSA, the stabilizing agent of choice for use in the practice of the present invention, has been shown to improve survival and wellness when given as a supplement to patients receiving conventional forms of total nutrient admixtures.

7 Claims, No Drawings

OTHER PUBLICATIONS

Chen et al., "Comparison of albumin and casein microspheres as a carrier for doxorubicin," *J. Pharm. Pharmacol.*, 39:978–985 (1987).

Feinstein et al., "Two–Dimensional Contrast Echocardiography. I. In Vitro Development and Quantitative Analysis of Echo Contrast Agents," *JACC*, 3(1):14–20 (1984).

Grinstaff & Suslick, "Nonaqueous Liquid Filled Microcapsules," *Polym. Prepr.*, 32:255–256 (1991).

Gupta et al., "Albumin microspheres. III. Synthesis and characterization of microspheres containing adriamycin and magnetite," *International Journal of Pharmaceutics*, 43:167–177 (1988).

Ishizaka et al., "Preparation of Egg Albumin Microcapsules and Microspheres," *Journal of Pharmaceutical Sciences*, 70(4):358–363 (1981).

Klibanov et al., "Amphipathic polyethyleneglycols effectively prolong the circulation time of liposomes," *FEBS*, 268(1):235–237 (1990).

Koenig & Meltzer, "Effect of Viscosity on the Size of Microbubbles Generated for Use as Echocardiographic Contrast Agents," *Journal of Cardiovascular ultrasonography*, 5(1):3–4 (1986).

Leucuta et al., "Albumin microspheres as a drug delivery system for epirubicin: pharmaceutical, pharmacokinetic and biological aspects," *International Journal of Pharmaceutics*, 41:213–217 (1988).

Molecular Biosystems, Inc., "Albunex≃—Preclinical Investigator's Package".

Moseley et al., "Microbubbles: A Novel MR Susceptibility Contrast Agent," 10th Annual Meeting of Society of Magnetic Resonance in Medicine (1991).

Suslick & Grinstaff, "Protein Microencapsulation of Nonaqueous Liquids," *J. Am. Chem. Soc.*, 112(21):7807–7809 (1990).

Willmott & Harrison, "Characterisation of freeze–dried albumin microspheres containing the anti–cancer drug adriamycin," *International Journal of Pharmaceutics*, 43:161–166 (1988).

——, "Serum Albumin Beads: An Injectable, Biodegradable System for the Sustained Release of Drugs," *Science*, 213(10):233–235 (1981).

* cited by examiner

TOTAL NUTRIENT ADMIXTURES AS STABLE MULTICOMPONENT LIQUIDS OR DRY POWDERS AND METHODS FOR THE PREPARATION THEREOF

RELATED APPLICATIONS

This application is a continuation-in-part of U.S. Ser. No. 08/412,726, filed Mar. 29, 1995, now U.S. Pat. No. 5,560,933, which is, in turn, a divisional of U.S. Ser. No. 08/023,698, filed Feb. 22, 1993, now issued as U.S. Pat. No. 5,439,686, the entire contents of both of which are hereby incorporated by reference herein in their entirety.

FIELD OF THE INVENTION

The present invention relates to stabilized liquid and solid compositions useful as total nutrient admixtures (TNA), as well as methods for the preparation thereof. Invention compositions are easily reconstituted with water to form multicomponent or three-in-one TNA compositions (i.e., containing fat emulsions, dextrose, and amino acids with electrolytes) suitable for parenteral administration of nutrition.

BACKGROUND OF THE INVENTION

Dextrose and amino acids have been the major components of glucose-based parenteral nutrition systems, with an optimal infusion rate of approximately 400 grams of dextrose per day for a 70-kg person. The addition of intravenous fat emulsions has improved patient care by preventing the development of essential fatty acid deficiencies, and by providing a calorically dense product to supplement non-protein calories. Traditionally, intravenous fat emulsions have been infused separately from the parenteral nutrition solution (see Warshawsky in Nutrition in Clinical Practice 7:187–196 (1992)).

Lipid for intravenous infusion was originally introduced as a 10% isotonic emulsion (Intralipid) which allowed total parenteral nutrition (TPN) to be administered via a peripheral vein, thereby reducing the complications associated with central venous administration. The lipid emulsion also provided a safe and effective method for administering essential fatty acids to patients receiving glucose from TPN.

More recently, the total nutrient admixture (TNA) system was developed, in which a commercial emulsion (such as Intralipid), amino acid solution, glucose, electrolytes, and trace minerals are mixed in one flexible-container for safer and more convenient administration. The mixture is prepared in the hospital pharmacy prior to use, and is desirably administered within 24 hours of preparation (see Warshawski in Nutrition in clinical practice 7:187–196 (1992)). The order of mixing the various components is crucial, due to the inherent instability of the fat emulsion in the presence of electrolytes and amino acids. Most conservative guidelines for prolonged TNA storage are 7 days at 4° C., or up to 24 hours at room temperature. When TNAs are prepared, the dextrose, amino acids and additives should be admixed first, and the fat emulsion should be added last, while the sterility of the system is maintained. Typical TNA formulations are composed of dextrose, triglycerides, amino acids, vitamins, trace elements and electrolytes (such as, for example, sodium and potassium chlorides; calcium, magnesium, sodium and potassium phosphates, and the like).

Commercially available TNA systems include the "All-In-One TPN Mixing System" from KabiVitrum, and the "3-in-1 Admixture System" from Travenol Laboratories. In each of these commercially available products, all components, including the emulsion, should be mixed shortly prior to use. Although these TNA systems represent significant improvements over older methods, some controversy still remains regarding the stability and clinical application of these admixture systems (see Brown, et al., in Journal of Parenteral and Enteral Nutrition 10:650–658 (1986)). Indeed these TNAs have to be used within a very short time after mixing all components.

Currently available total nutrient admixtures, i.e., mixtures which are prepared prior to their administration, have significantly reduced overall hospital costs associated with both preparation and administration, because the preparation and administration of conventional parenteral nutrients is time consuming. For example, the time spent on the preparation of conventional total parenteral nutrition (TPN, i.e., a mode of treatment wherein the fat emulsion is administered separately) ranges from about 13 minutes for each adult formula to about 49 minutes for each pediatric formula.

As health care costs have continued to escalate, practitioners have begun to search for ways to reduce costs, while maintaining quality patient care. For example, in pediatric patients, the cost of preparation and administration of the TNA system is less than half that of the TPN system. The potential savings is even greater with adult patients, who typically require two to three times greater daily volume of parenteral nutrition, as compared with pediatric patients (see, for example, Warshawsky in Nutrition in Clinical Practice 7:187–196 (1992)).

Fat emulsions, which are one component of TNA compositions, are classified as the "oil-in-water" type (as opposed to "water-in-oil" type). An emulsion is a twophase system in which one immiscible liquid (the internal dispersed phase) is dispersed in the form of small droplets throughout another immiscible liquid (the external continuous phase) by means of emulsifying agents or surfactants (e.g., phospholipids). Several commercially available fat emulsions utilize egg phospholipids as surfactants. The emulsifying agents may form a physical barrier, mainly due to electrostatic repulsion at the interface between the tiny droplets of the oil phase, to prevent the dispersed droplets from coalescing and eventually reverting to two continuous undispersed phases. The barrier produced by the emulsifying agent can take the form of a mechanical interfacial film or an electrostatic repulsion or both.

The emulsifying agent which is commonly used to in stabilize fat emulsions for parenteral nutrition is lecithin (which is obtained from natural sources, e.g., egg yolk). Lecithin comprises a mixture of phospholipids, of which phosphatidylcholine is the most abundant. Since pure phospholipid emulsifiers provide only poor stability, certain ionic lipids (such as phosphatidic acid and phosphatidyl serine) are required in order to increase the electrostatic-repulsive properties and enhance the mechanical barrier by forming liquid crystalline gel structures at the oil-water interface (Brown, et al., Journal of Parenteral and Enteral Nutrition 10:650–658 (1986)).

The pH of an emulsion is an important consideration in determining the stability of phospholipid based emulsions. Fat emulsions are generally most stable at their manufactured pH (about 8.0), and any additives which severely alter pH (such as dextrose, a component of TNA compositions) may adversely affect emulsion stability. Dextrose solutions are acidic and can significantly decrease the pH of lipid emulsions, with resultant loss of stability. As the pH decreases (to about 2.5), the emulsifying agent becomes electrically neutral and its desirable repulsive forces are lost.

In addition, one of the mechanisms for destabilization of phospholipid-based emulsions is the hydrolysis of phospholipid, which releases fatty acids and phosphatidic acid into the aqueous phase of the emulsion. This likely causes a decrease in pH, thus causing a decrease in Zeta potential of emulsion droplets, and hence coalescence and phase separation (see Magdassi et al., in *J. Disp. Sci. Techi.* 12:69–82 (1991)).

The addition of electrolytes, e.g., multivalent cations such as calcium ions, can profoundly reduce the surface potential, thereby leading to decreased repulsion between emulsion droplets and ultimately coalescence of the emulsion. Since typical TNA compositions contain several electrolytes, their presence also leads to instability of the emulsion.

Thus, TNA compositions (i.e., compositions containing fat emulsions, dextrose, amino acids and electrolytes) are inherently of limited stability due to the nature of phospholipid-based emulsions. Thus, there clearly exists a need in the art for stable TNA compositions and methods for the preparation thereof.

BRIEF DESCRIPTION OF THE INVENTION

Thus it is an object of this invention to provide a stabilized total nutrient admixture composition for parenteral administration which is stable for long periods of transportation or storage in the form of a dry lyophilized powder.

It is a further object of the present invention to provide stabilized oil-in-water emulsions for parenteral administration. Invention compositions are stabilized by protein(s) (such as human serum albumin), and can readily be lyophilized. The resulting lyophilized material can be reconstituted easily by adding sterile water thereto immediately before use.

It is yet another object of the invention to provide a stabilized composition for nutrient parenteral administration which contains fat, dextrose, amino acids, and electrolytes as a 3-in-1 complete-nutrition composition.

It is still another object of this invention to provide stabilized TNA compositions for parenteral administration using human serum albumin as the stabilizer and as a nutritional supplement to maintain proper circulatory oncotic pressure.

It is a further object of this invention to provide a stabilized solid form nutrient supplement, in which human serum albumin serves, in addition to the functions noted above, as a reconstitution aid and as a cryoprotectant agent. Therefore, nutritional compositions can be formed by omitting one or more of the above-described components. In addition, various combinations of compositions which contain human serum albumin, together with components such as iron derivatives, glucose and additional electrolytes, can also be formed.

It is yet another object of this invention to provide a stable dispersion of oil in an aqueous phase for parenteral administration using human serum albumin as the stabilizer and as a nutritional supplement to maintain proper circulatory oncotic pressure.

These and other objects of the invention will become apparent upon review of the specification and claims.

Thus, in accordance with the present invention, there are provided stable Total Nutrient Admixture (TNA) compositions suitable for parenteral administration. In addition, also provided are lyophilized compositions which are easily reconstituted with water to form TNA compositions suitable for injection.

In accordance with another aspect of the present invention, we have discovered that the stability problems associated with the use of conventional monomeric surfactants (e.g., phospholipids) can be solved by the use of the protein human serum albumin (HSA) as the stabilizer against coalescence of the oil droplets. HSA is particularly advantageous in that it can safely be administered I.V.

TNA compositions of the present invention are prepared by combining all components (e.g., oil, dextrose, amino acids, electrolytes, and the like) in a single dispersion step. This dispersion is performed in equipment capable of producing high shear and cavitation forces, such as a high pressure homogenizer or a sonicator.

In accordance with another embodiment of the present invention, we have developed compositions useful for in vivo delivery of substantially water insoluble pharmacologically active agents. Invention compositions comprise substantially water insoluble pharmacologically active agents (as a solid or liquid) contained within a polymeric shell. The polymeric shell is a biocompatible polymer, crosslinked by the presence of disulfide bonds. The polymeric shell, containing substantially water insoluble pharmacologically active agents therein, is then suspended in a biocompatible aqueous liquid for administration.

Administering serum albumin at high concentration appears to be associated with a reduction in hospital morbidity in hypoalbuminemic patients receiving central TPN. It is common practice to add normal serum albumin to the TPN formula in doses of 12.5 or 25 g/L in patients with hypoalbuminemia. Without supplementation, the serum albumin level rises very slowly. In contrast, adequately raising the serum albumin level through supplementation restores the normal plasma osmotic pressure and circulatory volume (see, for example, Brown et al., in Critical Care Medicine 16:1177–1182 (1988)). Therefore, the use of albumin as the stabilizing agent in the practice of the present invention may also provide additional medical benefit.

The many added advantages of the present invention are expected to further reduce the costs associated with the use of TNA compositions, since the lyophilized powder can be transported and stored for great lengths of time without loss of stability, the 3-in-1 dry powder can be instantly reconstituted at the point of use with sterile water, and the resulting composition can be injected as a single component into a peripheral vein, even at the patient's home, without the need for a hospital pharmacy. The use of powdered TNA compositions clearly simplifies the preparation procedure (one need add only water for reconstitution), and minimizes the risk of errors and possible contamination.

DETAILED DESCRIPTION OF THE INVENTION

In accordance with the present invention, there are provided methods for the stabilization of total nutrient admixture (TNA) compositions, said method comprising subjecting a mixture comprising:

submicron oil droplets stabilized by coating with a biocompatible polymer(s), and aqueous medium containing sugars, amino acids and electrolytes, and optionally one or more additives selected from the group consisting of calcium sequestering agents, water, water-soluble vitamins, water-soluble trace elements, stabilizers, agents of therapeutic value and oil-soluble vitamins, to high shear and cavitation forces, thereby producing a stabilized TNA composition. In accordance with the present invention, the desired exposure to high shear and cavitation conditions can be provided in a variety of ways, for example, by exposing the above-described mixture to high shear and cavitation forces in a high pressure homogenizer, by subjecting the above-described mixture to ultrasonic irradiation, and the like. The average diameter of oil droplets prepared in accordance with the present invention is typically no greater than about 400 nm, and the diameter of such oil droplets is typically no greater than about 10 microns.

In accordance with another embodiment of the present invention, there are provided methods for the preparation of stable TNA compositions, said method comprising subjecting a mixture comprising:

submicron oil droplets stabilized by coating with a biocompatible polymer(s), and aqueous medium containing sugars, amino acids and electrolytes, and optionally one or more additives selected from the group consisting of calcium sequestering agents, water, water-soluble vitamins, water-soluble trace elements, stabilizers, agents of therapeutic value and oil-soluble vitamins, to high shear and cavitation forces, thereby producing a stabilized TNA composition.

In accordance with yet another embodiment of the present invention, there are provided stabilized TNA compositions useful for in vivo parenteral delivery of pharmacologically acceptable lipids or fats, wherein said composition comprises submicron droplets of lipid or fat stabilized by coating with a biocompatible polymer, wherein said lipid or fat is a solid or liquid, and wherein the largest cross-sectional dimension of said stabilized droplets is no greater than about 10 microns.

As used herein, the term "in vivo delivery" refers to delivery of TNA compositions by such routes of administration as oral, intravenous, subcutaneous, intraperitoneal, intrathecal, intramuscular, inhalational, topical, transdermal, suppository (rectal), pessary (vaginal), and the like.

As used herein, the term "micron" refers to a unit of measure of one one-thousandth of a millimeter.

As used herein, the term "biocompatible" describes a substance that does not appreciably alter or affect in any adverse way, the biological system into which it is introduced.

Examples of agents of nutritional value contemplated for use in the practice of the present invention include amino acids, sugars (e.g., dextrose, sucrose, and the like), proteins (e.g., albumin, insulin, hemoglobin, lysozyme, immunoglobulins, α-2-macroglobulin, fibronectin, vitronectin, fibrinogen, and the like), carbohydrates, water-soluble vitamins (e.g., vitamin C, B-complex vitamins, and the like), fat-soluble vitamins (e.g., vitamins A, D, E, K, and the like), calcium sequestering agents (e.g., citrate, EDTA, EGTA, and the like), electrolytes, water-soluble trace elements, fat, agents of therapeutic value (e.g., iron gluconate, calcium gluconate, and the like), and the like, or combinations of any two or more thereof.

A number of biocompatible polymers may be employed in the practice of the present invention for the formation of stabilized droplets which are an important component of stabilized TNA compositions of the invention. Essentially any polymer, natural or synthetic, optionally bearing sulfhydryl groups or disulfide bonds within its structure may be utilized for the preparation of the above-described stabilized droplets. The optional sulfhydryl groups or disulfide linkages may be preexisting within the polymer structure or they may be introduced by a suitable chemical modification. For example, natural polymers such as proteins, oligopeptides, polynucleic acids, polysaccharides (e.g., starch, cellulose, dextrans, alginates, chitosan, pectin, hyaluronic acid, and the like), and so on, are candidates for such modification.

A presently preferred protein for use in the practice of the present invention is albumin. optionally, proteins such as α-2-macroglobulin, a known opsonin, could be used to enhance uptake of the shell encased particles of substantially water insoluble pharmacologically active agents by macrophage-like cells, or to enhance the uptake of the shell encased particles into the liver and spleen.

The proteins of the present invention are capable of forming a steric barrier around each oil droplet, resulting in steric stabilization and prevention of coalescence of the oil droplets. In addition, the charged amino acid residues in the protein molecule cause electrostatic repulsion between approaching droplets, and therefore facilitates the preparation of very stable TNA compositions.

The steric barrier is maintained even at pH close to the isoelectlic point of the proteins (i.e., pH at which the protein has no residual charge) and also at the high electrolyte concentrations inherent in TNA compositions. In comparison, phospholipid based emulsions are unstable under these conditions.

In addition, HSA is capable of binding calcium ions (which are present in TNA compositions) and other multivalent cations. As a result, the stability problems associated with charge neutralization due to the presence of free multivalent ions are minimized. In comparison, phospholipid based emulsions are unstable in the presence of multivalent cations.

The proteins (e.g., HSA) also have a buffering capacity, which helps to maintain the pH of the formulation above the isoelectric point of the protein, hence making the TNA composition much less sensitive to pH changes. This represents a significant advantage over the phospholipid based emulsions which are currently used as a component of TNA. The buffering capacity of the protein in the present TNA composition decreases the deleterious effects of low-pH dextrose.

Human serum albumin (HSA) is also capable of binding fatty acids (which are intermediates in fat metabolism), amino acids (such as tryptophan), and vitamins (which are often added to TNA compositions, e.g., Vitamins B, C and D, see Peters in "all about albumin" Academic Press (1996)). Therefore, the use of HSA as the stabilizing agent in the practice of the present invention offers significant advantages over the conventional TNA (which is obtained by mixing the aqueous soluble components with a plhospholipid based emulsion).

The protein serves as a stabilizing agent to suspend the lipid or fat within a larger aqueous phase, which contains dextrose, amino acids and electrolytes. The presence of protein also permits lyophilization of the oil-in-water emulsion without loss of chemical stability or phase separation, and provides an osmotic-pressure-regulating effect to the bloodstream.

The droplet size obtained by homogenizing all components in one step, under conditions of high shear forces, is between 50–1500 nm, preferably between 100–400 nm, which is a suitable size to allow intravenous injection. As demonstrated in the following examples, the TNA compositions obtained by the invention method are very stable, and meet the requirements of stability set forth by the industry, i.e, at least one week at 4° C., followed by 24 hrs. at room temperature, without oil separation or a significant change in droplet size. The external aqueous phase contains dextrose, amino acids and electrolytes, which are reduced to powder or crystalline form by lyophilization, and which are reconstituted to a biologically compatible aqueous phase immediately before use simply by adding sterile nonpyrogenic water to the dry lyophilized powder. This dry form of the TNA is stable for a prolonged time, and after reconstitution, the liquid TNA has the same properties as the original TNA composition prior to lyophilization.

Similarly, synthetic polypeptides containing cysteine residues are also good candidates for formation of a stabilized droplets which are an important component of stabilized TNA compositions of the invention. In addition, polyvinyl alcohol, polyhydroxyethyl methacrylate, polyacrylic acid, polyethyloxazoline, polyacrylamide, polyvinyl pyrrolidinone, and the like, are good candidates for chemical modification (to introduce optional sulfhydryl and/or disulfide linkages) and shell formation (by causing the crosslinking thereof).

Oil droplets contemplated for formation in accordance with the present invention can be formed from a wide variety of organic media, including coconut oils, cotton seed oils, vegetable oils (soybean oil, olive oil, safflower oil, cotton seed oil, and the like), aliphatic, cycloaliphatic or aromatic hydrocarbons having 4–30 carbon atoms, aliphatic or aromatic alcohols having 2–30 carbon atoms, aliphatic or aromatic esters having 2–30 carbon atoms, alkyl, aryl, or cyclic ethers having 2–30 carbon atoms, alkyl or aryl halides having 1–30 carbon atoms, optionally having more than one halogen substituent, ketones having 3–30 carbon atoms, polyalkylene glycol, or combinations of any two or more thereof.

Particles of invention stabilized TNA compositions, prepared as described above, are delivered as a suspension in a biocompatible aqueous liquid. This liquid may be selected from water, saline, a solution containing appropriate buffers, a solution containing nutritional agents such as amino acids, sugars, proteins, carbohydrates, vitamins or fat, and the like.

In accordance with another embodiment of the present invention, there is provided a method for the preparation of stabilized TNA compositions.

The preparation of invention compositions involves the following three steps:
  a. mixing a suitable biocompatible polymer (e.g., human serum albumin) with a solution of amino acids, sugars (e.g., dextrose) and electrolytes required for parenteral nutrition formulations, and optionally with a calcium sequestering agent such as sodium citrate,
  b. adding a suitable oil (e.g., soybean oil) and homogenizing the mixture using equipment which creates high shear forces, to obtain a submicron emulsion in which the droplet size is in the range of 150–250 nm, and the aqueous phase contains the water soluble nutrient ingredients. The biocompatible polymer (e.g., human serum albumin) coats the oil droplets, and a small fraction remains free in the aqueous phase, and
  c. water is optionally removed from the resulting liquid TNA by suitable methods, such as lyophilization, and a solid, white cake is obtained, within 48–72 hours of lyophilization.

The resulting solid TNA can easily be reconstituted upon addition of water, even after prolonged storage, to yield a liquid TNA which has properties similar to that of the liquid TNA prior to lyophilization.

Those skilled in the art will recognize that several variations are possible within the scope and spirit of this invention. As readily understood by those of skill in the art, the organic media employed for the preparation of stabilized droplets in accordance with the present invention may be varied, a large variety of pharmacologically active agents may be utilized, and a wide range of proteins as well as other natural and synthetic polymers may be used in the formation of the above-described stabilized droplets. Applications are also fairly wide ranging. Other than biomedical applications such as the delivery of drugs, diagnostic agents (in imaging applications), artificial blood and parenteral nutritional agents, the stabilized droplets described herein may be incorporated into cosmetic applications such as skin creams or hair care products, in perfumery applications, in pressure sensitive inks, and the like.

The invention will now be described in greater detail by reference to the following non-limiting examples.

EXAMPLE 1

The purpose of this example is to demonstrate the ability of human serum albumin to facilitate the formation and stabilization of submicron oil droplets. Thus, 40 ml of 2.5% HSA solution (pH 7) were pre-homogenized for 5 minutes at 15,000 rpm (Vitris, model Tempest I.Q.). The resulting liquid was transferred into a high pressure homogenizer, and was homogenized continuously for 10 minutes at 18,000 psi (Avestin high pressure homogenizer), while cooling the circulating liquid through a heat exchanger at 0° C. The average diameter of the resulting droplets (by number distribution) is 219 nm. After storage at 4° C. for 137 days, there were no signs of oil separation or of creaming, and the droplet size remained practically unchanged, 190–220 nm.

EXAMPLE 2

15 ml of 10% amino acid solution for injection (10% FreAmine III, McGaw), 4.3 ml of 70% dextrose solution for injection (McGaw), 0.5 ml phosphate buffer (0.147M), 0.4 ml KCl (2M), NaCl (4M), 0.5 ml $MgSO_4$ (0.406M), 0.5 ml sodium citrate (10%), 0.5 ml calcium gluconate (0.46M), were mixed with 0.25 grams of HSA (Bayer), until a clear solution was obtained. The solution (total volume 22.5 ml) was filtered through a 0.22 μm filter. Then, 2.5 ml soybean oil (Croda) was added to the aqueous solution, and the mixture was homogenized for 5 minutes at 15,000 rpm (Vitris, model Tempest I.Q.). This crude emulsion was further subjected to high pressure homogenization at 18,000 psi while recycling the emulsion for 10 minutes (Avestin high pressure homogenizer) The emulsion was passed during the cycles through a heat exchanger at −8° C. The average droplet diameter size (by number) is 205 nm (measured by Malvern, model Zetasizer 4, at 90° C.), and the pH of the final emulsion is 5.8. The emulsion was stored under nitrogen in a polypropylene test tube, for one week at 4° C., followed by one day at room temperature (~21–24° C.). The droplet size was not changed, and there were no signs of oil separation or creaming.

It was found that this TNA composition could be sterile-filtered (0.22 μm filter, ca uStar), after 1:1 dilution with water (in order to bring the concentration of all components to that required for a "low dextrose" formulation), thus preventing the need to autoclave the final composition. This is a significant advantage, since sterilization under high temperature (as performed for conventional fat emulsions used in TNA) cause browning of the TNA due to the presence of dextrose and amino acids. For comparison, it was impossible to sterile-filter a commonly available TNA composition, in which all components are mixed.

After storage of this TNA composition for 110 days, the droplet size remained practically unchanged (196 nm), and there were no signs of oil separation or even creaming. This finding indicates the very high stability of the TNA formed using HSA, in the liquid composition, in spite of the presence of electrolytes.

EXAMPLE 3

A TNA composition was prepared according to the procedure set forth in Example 2. The resulting TNA was frozen rapidly by immersing a glass vial which contained the sample in liquid nitrogen. The frozen sample was lyophilized (Labconco) for 72 hours, yielding a white, solid, homogeneous material. Upon addition of sterile water to the solid material, immediate reconstitution is observed, yielding a TNA composition which has a milky appearance, similar to that of the liquid TNA. The average droplet size after reconstitution was very similar to the size before lyoplilization, ~200–235 nm.

EXAMPLE 4

A TNA formulation was prepared according to the procedure employed for the preparation of the composition set forth in Example 2, with two changes: No sodium citrate (i.e., the calcium sequestering agent) was employed in the aqueous phase, and the oil phase contained 10% ethanol. The emulsion was prepared as previously described, while the high pressure homogenizing valve was also cooled by an ice-water mixture. The resulting emulsion has an average diameter (by number distribution) of 120–140 nm. This TNA composition could be filtered through a 0.45 $\mu$m filter (millipore syringe filter), and then by a 0.22 $\mu$m filter (millipore syringe filter), without significant change in the size of the oil droplets and the appearance of the formulation.

When preparation of the same formulation is repeated, but without the introduction of ethanol into the oil phase, the average diameter (by Number) is somewhat higher, i.e., 160–180 nm.

EXAMPLE 5

This example demonstrates the high stability and ease of reconstitution of the human serum albumin-based TNA compositions of the invention, when prepared in the solid, ready to use form. Thus, a TNA was prepared according to the procedure set forth in Example 2, while the amount of HSA was increased to 1 g. Thus, the concentration of HSA in the TNA was 4% w/v and the pH of the solution was adjusted to 7.

The oil droplets of the resulting liquid composition were in the submicron range, and the average diameter size (by number distribution) was 168 nm. The sample was filtered through a 0.45 $\mu$m filter, and was frozen by liquid nitrogen. Then, the sample was lyophilized for 72 hours to give a white, solid material.

The solid sample was stored for 82 days at 4° C. After this period, sterile water was added to the solid sample. Immediate reconstitution was obtained, and the sample had a milky appearance similar to that of the original liquid TNA. The average diameter size was very similar to the original size, 170 nm.

EXAMPLE 6

A TNA composition was prepared according to the procedure described in Example 4, except without the use of ethanol. Thus, 2 ml of the liquid TNA were injected I.V. daily, to a rat which had previously received a suitable dose of the anti-cancer drug, paclitaxel. As a control, 2 ml of saline solution were injected daily to another rat which had received the same treatment. Both rats were fed similarly and were injected daily for 8 days.

It was found that the rat which received the saline solution constantly lost body weight; at day 8 the total weight loss was 3.1%. In contrast, the rat which received the TNA formulation experienced a steady increase in body weight; at day 8 the total increase in body weight was 5.7%. In addition, it was found that the hemoglobin level after 5 days decreased by 16.4% for the control animal, while it increased by 4.1% for the rat which received the TNA.

This example demonstrates that the rat which received TNA compositions according to the present invention recovered much faster than the rat which did not receive any TNA composition, and indicates the benefits of the invention formulations.

While the invention has been described in detail with reference to certain preferred embodiments thereof, it will be understood that modifications and variations are within the spirit and scope of that which is described and claimed.

That which is claimed is:

1. A stabilized total nutrient admixture (TNA) composition useful for in vivo parenteral delivery of a pharmacologically acceptable lipid or fat, said composition comprising:

submicron droplets of lipid or fat stabilized by intimate association with a biocompatible polymer, wherein said lipid or fat is a solid or liquid, and wherein the diameter of said stabilized droplets is no greater than about 10 microns, sugars, amino acids, electrolytes, and optionally, one or more additives selected from the group consisting of calcium sequestering agents, water, water-soluble vitamins, water-soluble trace elements, stabilizers, agents of therapeutic value and oil-soluble vitamins.

2. A composition according to claim 1 wherein the average diameter of said oil droplets is no greater than about 400 nm.

3. A stabilized TNA composition according to claim 1 wherein said stabilized droplets containing lipid or fat therein is suspended in biocompatible aqueous medium.

4. A composition according to claim 1 wherein said biocompatible polymer is a natural or synthetic protein, oligopeptide, polynucleic acid or polysaccharide.

5. A composition according to claim 4 wherein said protein is albumin, insulin, hemoglobin, lysozyme, immunoglobulins, $\alpha$-2-macroglobulin, fibronectin, vitronectin or fibrinogen.

6. A composition according to claim 4 wherein said protein is albumin.

7. A method for the delivery of a total nutrient admixture (TNA) composition to a subject, said method comprising administering to said subject an effective amount of composition according to claim 1.

* * * * *

UNITED STATES PATENT AND TRADEMARK OFFICE
CERTIFICATE OF CORRECTION

PATENT NO.  : 6,528,067 B1
DATED       : March 4, 2003
INVENTOR(S) : Magdassi et al.

It is certified that error appears in the above-identified patent and that said Letters Patent is hereby corrected as shown below:

<u>Title page, Item [60] and Column 1, line 8,</u>
The Related U.S. Application Data should read as follows:

Divisional application under 37 C.F.R. 1.53(b) of application No. 08/723,805, filed September 30, 1996, now pending, which is a continuation-in-part of application No. 08/412,726, filed March 29, 1995, now issued as U.S. Patent No. 5,560,933, which is a divisional of application No. 08/023,698, filed February 22, 1993, now issued as U.S. Patent No. 5,439,686.

Signed and Sealed this

Twenty-ninth Day of July, 2003

JAMES E. ROGAN
*Director of the United States Patent and Trademark Office*